(12) United States Patent
Xia

(10) Patent No.: US 10,458,233 B2
(45) Date of Patent: Oct. 29, 2019

(54) SENSORS FOR IN-SITU FORMATION FLUID ANALYSIS

(71) Applicant: Halliburton Energy Services, Inc., Houston, TX (US)

(72) Inventor: Hua Xia, Huffman, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 75 days.

(21) Appl. No.: 15/740,178

(22) PCT Filed: Dec. 29, 2016

(86) PCT No.: PCT/US2016/069208
§ 371 (c)(1),
(2) Date: Dec. 27, 2017

(87) PCT Pub. No.: WO2018/125138
PCT Pub. Date: Jul. 5, 2018

(65) Prior Publication Data
US 2018/0313214 A1 Nov. 1, 2018

(51) Int. Cl.
*G01N 29/02* (2006.01)
*G01N 29/12* (2006.01)
(Continued)

(52) U.S. Cl.
CPC ............ *E21B 49/082* (2013.01); *E21B 47/00* (2013.01); *E21B 49/08* (2013.01); *G01N 21/85* (2013.01);
(Continued)

(58) Field of Classification Search
CPC .. E21B 49/082; E21B 2049/085; E21B 47/00; E21B 49/08; G01N 35/1097;
(Continued)

(56) References Cited

U.S. PATENT DOCUMENTS 4,575,261 A 3/1986 Berger et al.
6,604,051 B1 8/2003 Morrow et al.
(Continued)

FOREIGN PATENT DOCUMENTS

EP 1254352 B1 8/2006
WO 2015137915 A1 9/2015

OTHER PUBLICATIONS

Chiasson, Andrew D. "Thermal response testing of geothermal wells for downhole heat exchanger applications." Proceedings of the Thirty-Seventh Workshop on Geothermal Reservoir Engineering, Stanford University, Stanford, CA, 2012.
(Continued)

*Primary Examiner* — Christopher P McAndrew
(74) *Attorney, Agent, or Firm* — Ben Fite; Baker Botts L.L.P.

(57) ABSTRACT

A downhole tool including a tube having an inner bore that receives a sample of fluid from a subterranean formation, a vibration source and a vibration receiver each at least partially coupled to the tube, and a controller coupled to the vibration source and the vibration receiver is provided. In situ measurements of thermo-physical properties including, but not limited to, fluid density/viscosity, thermal conductivity and heat capacity, and hydrocarbon molecular weight may be provided through the system. The vibrating sensor may include a sensor platform that can be incorporated into sensors purpose built to test different in situ thermo-physical properties that are technically difficult or expensive to test using typical sensors. The vibrating sensors may be modularized and incorporated as a suite of in situ downhole sensors into existing downhole fluid sampling tools, reducing the overall expense of in situ testing.

20 Claims, 8 Drawing Sheets

(51) Int. Cl.
| | |
|---|---|
| *G01N 29/22* | (2006.01) |
| *G01N 29/265* | (2006.01) |
| *G01N 29/036* | (2006.01) |
| *G01N 35/10* | (2006.01) |
| *G01N 33/28* | (2006.01) |
| *E21B 49/08* | (2006.01) |
| *E21B 47/00* | (2012.01) |
| *G01N 21/85* | (2006.01) |

(52) U.S. Cl.
CPC ........... *G01N 29/02* (2013.01); *G01N 29/036* (2013.01); *G01N 29/12* (2013.01); *G01N 29/225* (2013.01); *G01N 29/265* (2013.01); *G01N 35/1097* (2013.01); *E21B 2049/085* (2013.01); *G01N 33/2823* (2013.01); *G01N 2291/014* (2013.01); *G01N 2291/102* (2013.01); *G01N 2291/2636* (2013.01)

(58) Field of Classification Search
CPC .... G01N 29/036; G01N 21/85; G01N 29/265; G01N 29/225; G01N 29/12; G01N 29/02; G01N 2291/102; G01N 2291/014; G01N 2291/2636; G01N 33/2823
USPC ......................................................... 324/366
See application file for complete search history.

(56) References Cited

U.S. PATENT DOCUMENTS

| | | |
|---|---|---|
| 6,850,847 B2 | 2/2005 | Morrow et al. |
| 6,877,332 B2 | 4/2005 | DiFoggio |
| 6,912,904 B2 | 7/2005 | Storm, Jr. et al. |
| 6,925,392 B2 | 8/2005 | McNeill, III et al. |
| 7,217,367 B2 | 5/2007 | Huang et al. |
| 7,398,160 B2 | 7/2008 | Morrow et al. |
| 7,434,457 B2 | 10/2008 | Goodwin et al. |
| 7,526,953 B2 | 5/2009 | Goodwin et al. |
| 7,654,130 B2 | 2/2010 | Shah et al. |
| 7,752,885 B2 | 7/2010 | Huang |
| 7,937,999 B2 | 5/2011 | Blanz et al. |
| 7,959,865 B2 | 6/2011 | Schmidt et al. |
| 8,240,378 B2 | 8/2012 | Sonne et al. |
| 8,269,961 B2 | 9/2012 | Mostowfi et al. |
| 8,380,446 B2 | 2/2013 | Mostowfi et al. |
| 8,414,832 B1 | 4/2013 | Roques et al. |
| 8,453,732 B2 | 6/2013 | Sonne et al. |
| 8,492,152 B2 | 7/2013 | Jones et al. |
| 2002/0178803 A1 | 12/2002 | Pelletier et al. |
| 2005/0204808 A1 | 9/2005 | DiFoggio |
| 2005/0252307 A1 | 11/2005 | Andresen et al. |
| 2006/0233217 A1 | 10/2006 | Gleitman |
| 2009/0078461 A1* | 3/2009 | Mansure ................. E21B 36/04 175/17 |
| 2009/0189617 A1* | 7/2009 | Burns .................... E21B 43/24 324/649 |
| 2010/0241407 A1* | 9/2010 | Hsu ........................ G01N 11/16 703/2 |
| 2010/0268469 A1* | 10/2010 | Harrison ................ G01N 9/002 702/12 |
| 2011/0167910 A1* | 7/2011 | Storm ....................... G01F 1/74 73/32 A |
| 2011/0186353 A1* | 8/2011 | Turner ................. G05B 13/048 175/40 |
| 2011/0247878 A1 | 10/2011 | Rasheed |
| 2012/0072128 A1* | 3/2012 | Gao ........................ G01N 35/00 702/23 |
| 2013/0301389 A1* | 11/2013 | Alford .................... E21B 47/12 367/81 |
| 2013/0311099 A1 | 11/2013 | Eyuboglu et al. |
| 2013/0312481 A1 | 11/2013 | Pelletier et al. |
| 2014/0212983 A1 | 7/2014 | DiFoggio |
| 2015/0240614 A1* | 8/2015 | Allen ........................ E21B 7/00 175/40 |
| 2016/0003035 A1* | 1/2016 | Logan .................... E21B 47/12 340/854.6 |
| 2016/0108729 A1* | 4/2016 | Li ........................... G01N 11/16 702/12 |
| 2016/0154129 A1* | 6/2016 | Sayers .................... E21B 43/26 702/13 |
| 2016/0258279 A1 | 9/2016 | Xia et al. |

OTHER PUBLICATIONS

Chiasson, Andrew D. "Thermal response testing of geothermal wells for downhole heat exchanger applications." Geo-Heat Center, Oregon Institute of Technology, May 2012.

Kukkonen, I., et al. "Measurement of thermal conductivity and diffusivity in situ: measurements and results obtained with a test instrument." Working Report 25 (2000).

International Search Report and Written Opinion issued in related PCT Application No. PCT/US2016/069208 dated Nov. 6, 2017, 15 pages.

Search report issued in related French application No. 1761392, dated Feb. 5, 2019, 9 pages.

* cited by examiner

SENSORS FOR IN-SITU FORMATION FLUID ANALYSIS

CROSS-REFERENCE TO RELATED APPLICATION

The present application is a U.S. National Stage Application of International Application No. PCT/US2016/069208 filed Dec. 29, 2016, which is incorporated herein by reference in its entirety for all purposes.

BACKGROUND

This disclosure generally relates to downhole sensors, and more particularly to sensors for performing in-situ analyses of formation fluid properties.

Hydrocarbons, such as oil and gas, are commonly obtained from subterranean formations that may be located onshore or offshore. The development of subterranean operations and the processes involved in removing hydrocarbons from a subterranean formation are complex. Typically, subterranean operations involve a number of different steps such as, for example, drilling a wellbore through and/or into the subterranean formation at a desired well site, treating the wellbore to optimize production of hydrocarbons, and performing the necessary steps to produce and process the hydrocarbons from the subterranean formation. Some or all of these steps may utilize a reservoir model that permits a detailed characterization of the formation (e.g., its chemical composition, heterogeneity, multi-phase zones, fluid transport trend, etc.) to guide associated operations.

Thermo-physical properties of formation fluids may be used to formulate a reservoir model. Example thermo-physical properties include, but are not limited to, specific heat capacity, thermal conductivity, molecular weight, fluid density, viscosity, and mass diffusivity. In situ (i.e. downhole) measurements of these properties may be ideal to avoid phase changes within the formation fluids that occur when they are sent to the surface for testing. Yet, many of the thermo-physical properties (e.g., heat capacity, thermal conductivity, molecular weight) are typically determined in a laboratory due to the lack of capable downhole sensors. The resulting phase changes may reduce the accuracy of the corresponding measurements. Additionally, laboratory analysis may take days and weeks, adding time and expense to the operations.

BRIEF DESCRIPTION OF THE DRAWINGS

These drawings illustrate certain aspects of certain embodiments of the present disclosure. They should not be used to limit or define the disclosure.

Figure 1:
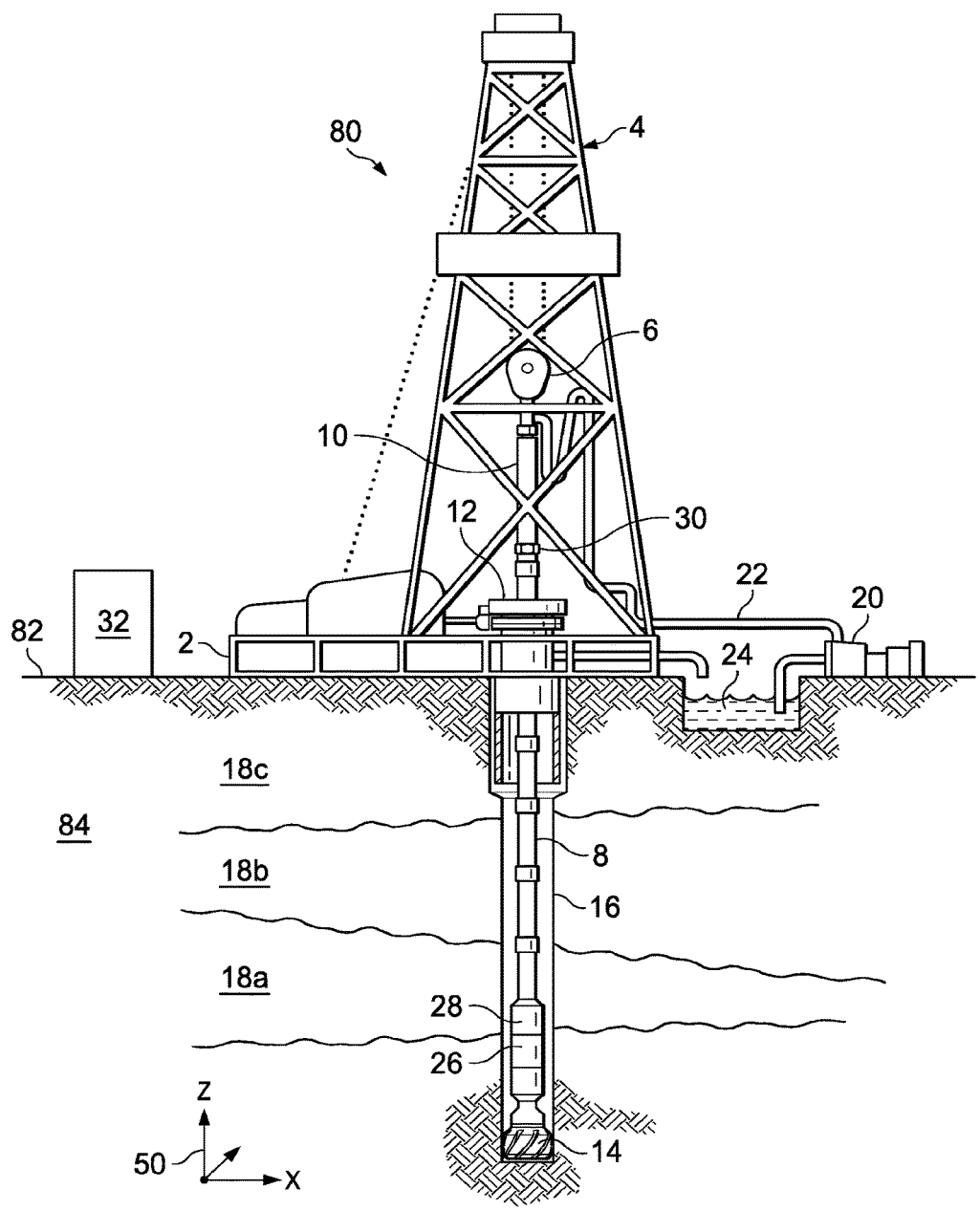
FIG. 1 is a diagram of an example subterranean drilling system, according to aspects of the present disclosure.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

Illustrative embodiments of the present disclosure are described in detail herein. In the interest of clarity, not all features of an actual implementation may be described in this specification. It will of course be appreciated that in the development of any such actual embodiment, numerous implementation-specific decisions are made to achieve the specific implementation goals, which will vary from one implementation to another. Moreover, it will be appreciated that such a development effort might be complex and time-consuming, but would, nevertheless, be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented using a tool that is made suitable for testing, retrieval and sampling along sections of the formation. Embodiments may be implemented with tools that, for example, may be conveyed through a flow passage in tubular string or using a wireline, slickline, coiled tubing, downhole robot or the like. "Measurement-while-drilling" ("MWD") is the term generally used for measuring conditions downhole concerning the movement and location of the drilling assembly while the drilling continues. "Logging-while-drilling" ("LWD") is the term generally used for similar techniques that concentrate more on formation parameter measurement. Devices and methods in accordance with certain embodiments may be used in one or more of wireline (including wireline, slickline, and coiled tubing), downhole robot (sessile or motile), MWD, and LWD operations.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

The terms "couple" or "couples" as used herein are intended to mean either an indirect or a direct connection. Thus, if a first device couples to a second device, that connection may be through a direct connection, or through an indirect mechanical or electrical connection via other devices and connections. Similarly, the term "communicatively coupled" as used herein is intended to mean either a direct or an indirect communication connection. Such connection may be a wired or wireless connection such as, for example, Ethernet or LAN. Such wired and wireless connections are well known to those of ordinary skill in the art and will therefore not be discussed in detail herein. Thus, if a first device communicatively couples to a second device, that connection may be through a direct connection, or through an indirect communication connection via other devices and connections.

According to aspects of the present disclosure, in situ measurements of thermo-physical properties including, but not limited to, fluid density/viscosity, thermal conductivity and heat capacity, and hydrocarbon molecular weight may be provided through one or more vibrating sensors, which may comprise a sensor platform that can be incorporated into sensors purpose built to test different in situ thermo-physical properties that are technically difficult or expensive to test using typical sensors. As will be described in detail below, the vibrating sensors may be modularized and incorporated as a suite of in situ downhole sensors into existing downhole fluid sampling tools, reducing the overall expense of in situ testing by leveraging existing technology. The vibrating sensors may also be deployed in a downhole fluid sampling tool dedicated to the determination of thermo-physical properties.

FIG. 1 is a diagram of a subterranean drilling system 80, according to aspects of the present disclosure. The drilling system 80 comprises a drilling platform 2 positioned at the surface 82. In the embodiment shown, the surface 82 comprises the top of a formation 18 containing one or more rock strata or layers 18a-c, and the drilling platform 2 may be in contact with the surface 82. In other embodiments, such as in an off-shore drilling operation, the surface 82 may be separated from the drilling platform 2 by a volume of water.

The drilling system 80 comprises a derrick 4 supported by the drilling platform 2 and having a traveling block 6 for raising and lowering a drill string 8. A kelly 10 may support the drill string 8 as it is lowered through a rotary table 12. A drill bit 14 may be coupled to the drill string 8 and driven by a downhole motor and/or rotation of the drill string 8 by the rotary table 12. As bit 14 rotates, it creates a borehole 16 that passes through one or more rock strata or layers 18. A pump 20 may circulate drilling fluid through a feed pipe 22 to kelly 10, downhole through the interior of drill string 8, through orifices in drill bit 14, back to the surface via the annulus around drill string 8, and into a retention pit 24. The drilling fluid transports cuttings from the borehole 16 into the pit 24 and aids in maintaining integrity or the borehole 16.

The drilling system 80 may comprise a bottom hole assembly (BHA) 50 coupled to the drill string 8 near the drill bit 14. The BHA 50 may comprise different combinations of drill collars; subs such as stabilizers, reamers, shocks, hole-openers; and various downhole tools, including, but not limited to, LWD/MWD systems, telemetry systems, downhole motors to drive the drill bit 14, and rotary steerable assemblies for changing the drilling direction of the drill bit 14. As depicted, the BHA 50 comprises a downhole fluid sampling tool 26 coupled to a telemetry system 28. The downhole fluid sampling tool 26 may comprise one or more vibrating sensors (not shown) that may take measurements used to determine certain thermo-physical properties of fluids within the formation 18. The telemetry system 28 may transfer measurements from the downhole fluid sampling tool 26 to a surface receiver 30 and/or to receive commands from the surface receiver 30 via a surface information handling system 32. The telemetry element 28 may comprise a mud pulse telemetry system, and acoustic telemetry system, a wired communications system, a wireless communications system, or any other type of communications system that would be appreciated by one of ordinary skill in the art in view of this disclosure. In certain embodiments, some or all of the measurements taken at the downhole fluid sampling tool 26 may also be stored within the downhole fluid sampling tool 26 or the telemetry element 28 for later retrieval at the surface 82 by the information handling system 32. The information handling system 32 may process the measurements taken by the downhole fluid sampling tool 26 to determine the associated thermo-physical properties, as will be described below. Alternatively, an information handling system within the BHA 50 (not shown) may determine the associated thermo-physical properties from the measurements.

In certain embodiments, the downhole fluid sampling tool 26 may be dedicated to the measurement of thermo-physical properties of formation fluids through the one or more vibrating sensors (not shown), or may include other types of sensors and/or electrical/hydraulic/mechanical systems that may, for instance, extract fluids from the formation for testing and/or perform measurements for properties of the formation fluids other than the thermo-physical properties discussed in this disclosure. In certain embodiments, as the bit 14 extends the borehole 16 through the formations 18, the downhole fluid sampling tool 26 may periodically collect measurements relating to the formation 18 and fluid trapped therein. For instance, the drilling process may be periodically paused so that the downhole fluid sampling tool 26 can extract and test/measurements fluid samples from the formation 18 to identify thermo-physical properties of the extracted fluids. The depth at which the fluids were extracted may be identified and associated with the corresponding measurements so that the formation 18 may be fully modeled.

Figure 2:
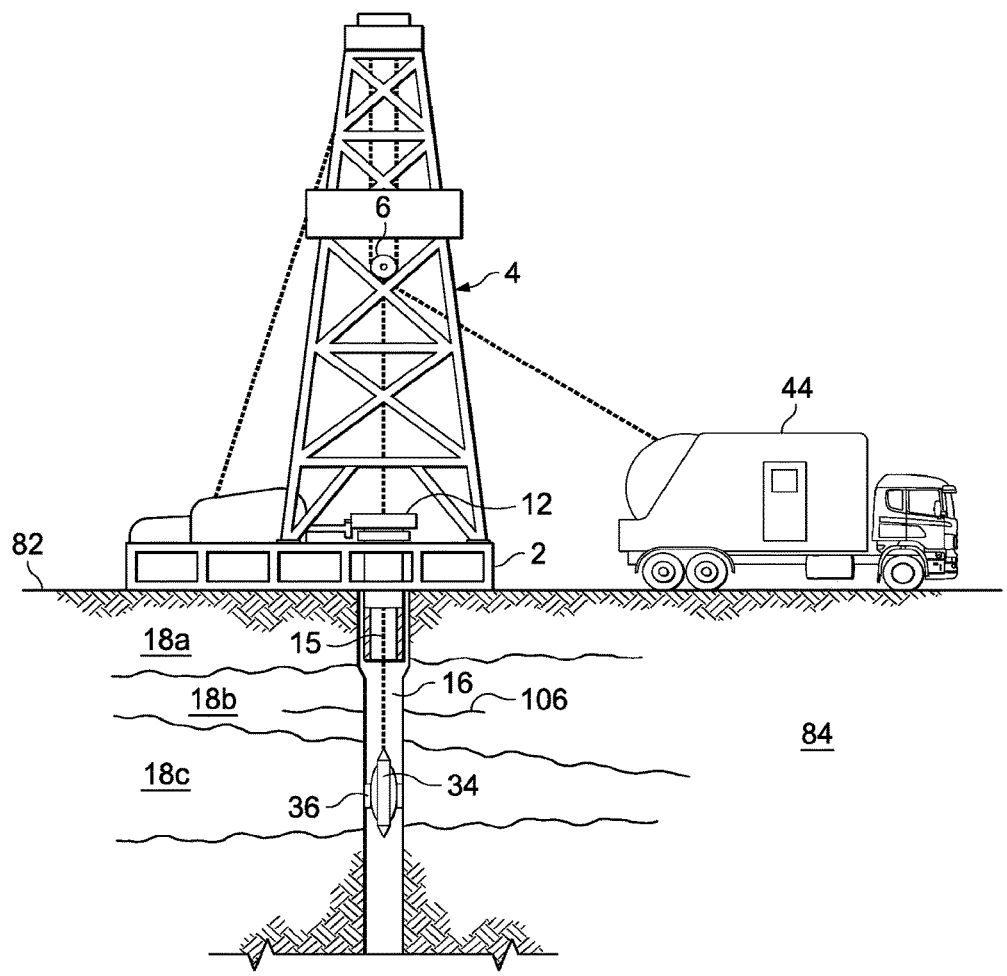
FIG. 2 is a diagram of an example subterranean drilling system with the drill string removed, according to aspects of the present disclosure.

At various times during the drilling process, the drill string 8 may be removed from the borehole 16 as shown in FIG. 2. Once the drill string 8 has been removed, measurement/logging operations can be conducted using a wireline tool 34, i.e., an instrument that is suspended into the borehole 16 by a cable 15 having conductors for transporting power to the tool from a surface power source, and telemetry from the tool body to the surface 102. The wireline tool 34 may comprise a downhole fluid sampling tool 36, similar to the downhole fluid sampling tool 26 described above. The tool 36 may be communicatively coupled to the cable 15. A logging facility 44 (shown in FIG. 2 as a truck, although it may be any other structure) may collect measurements from the tool 36, and may include computing facilities (including, e.g., a control unit/information handling system) for controlling, processing, storing, and/or visualizing the measurements gathered by the elements 36. The computing facilities may be communicatively coupled to the elements 36 by way of the cable 15. In certain embodiments, the control unit 32 may serve as the computing facilities of the logging facility 44.

Modifications, additions, or omissions may be made to FIGS. 1-2 without departing from the scope of the present disclosure. For instance, FIGS. 1-2 illustrate components of subterranean drilling and logging systems in a particular configuration, but other configurations are possible. Furthermore, fewer components or additional components beyond those illustrated may be included in the drilling and logging systems without departing from the scope of the present disclosure.

Vibrating sensors similar to those described herein may function as a platform through which sensors devoted to measuring one or more thermo-physical properties may be purpose built. For instance, at least one vibrating sensor may be incorporated into an in situ sensor that measures fluid density and viscosity of a formation fluid sample extracted from a formation. Other vibrating sensors may be incorporated into an in situ sensor configured to measure thermal conductivity and heat capacity and/or hydrocarbon molecular weight of formation fluid. These sensors may be reliably deployed within a downhole fluid sampling tool to provide in situ measurements of thermo-physical properties through which a reservoir may be characterized.

Figure 3:
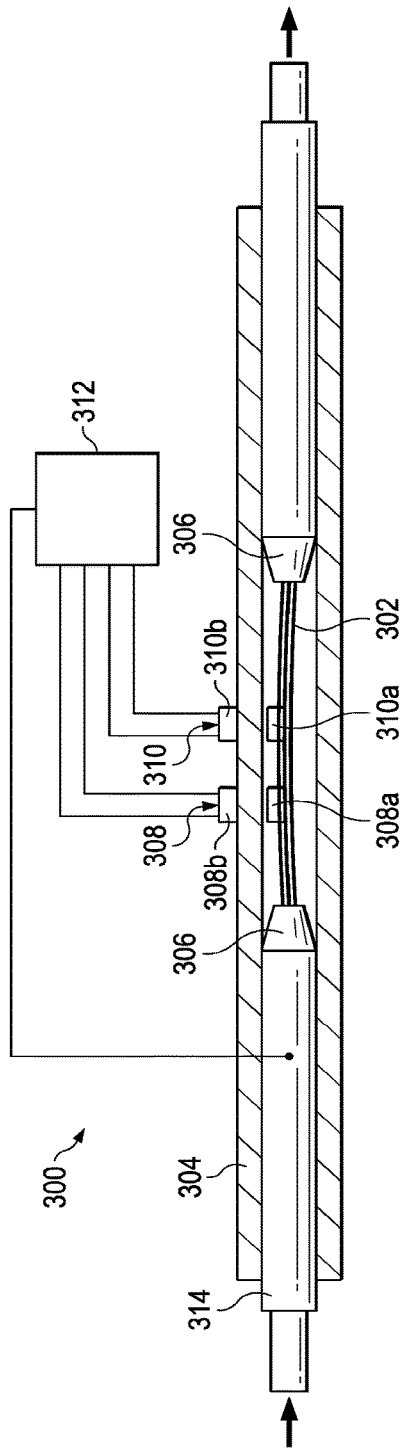
FIG. 3 is a diagram of an example density and viscosity sensor incorporating a vibrating sensor, according to aspects of the present disclosure.

FIG. 3 is a diagram of an example vibrating sensor 300, according to aspects of the present disclosure. The sensor 300 may be incorporated into one or more downhole fluid sampling tools, including those described above with reference to FIGS. 1 and 2, and those described in more detail below. As depicted, the vibrating sensor 300 comprises a tube 302 positioned within an outer housing 304 and secured to the housing 304 at both ends by anchors 306. The tube 302 may comprise an outer surface of diameter a, and an inner surface of diameter b that may define an internal flow bore 302a. The internal flow bore 302a may be placed in fluid communication with a fluid sample extracted from a formation, such as through a coupling between the sensor 300 and a pump-out system that will be described in detail below. The tube 302 may be made from one or more materials that allows for radial displacement of at least part of the tube 302. One example material includes, but is not limited to, titanium alloy.

The sensor 300 further comprises a vibration source 308 and a vibration receiver 310. Example vibration sources include electromagnetic, piezoelectric, mechanical, and hydraulic sources. As depicted, the vibration source 308 comprises an electromagnetic source in the form of a magnet 308a and coil assembly 308b, in which the magnet 308a is coupled to the tube 302 and the coil assembly 308b is coupled to the housing 304 in axial alignment with the magnet 308a. The vibration receiver 310 comprises a similar arrangement, in which a magnet 310a of the vibration sensor 310 is coupled to the tube 302 and a coil assembly 310b of the vibration sensor 310 is coupled to the housing 304 in axial alignment with the magnet 310a. These configurations are not intended to be limiting, however, as the type, orientation, and configuration of the vibration source 308 and vibration receiver 310 may differ depending on the embodiment. Additionally, in certain embodiments, the vibration source and sensor may be combined.

The vibration source 308 and vibration receiver 310 may be coupled to a controller 312. As used herein, a controller may include an information handling system or any other device that contains at least one processor configured to perform certain actions. Example processors include, but are not limited to, microprocessors, microcontrollers, digital signal processors (DSP), application specific integrated circuits (ASIC), or any other digital or analog circuitry configured to interpret and/or execute program instructions and/or process data. As depicted, the controller 312 is coupled to leads of the source coil 308a and leads of the sensor 310a. The controller 312 may function to trigger the vibration source 308 by connecting the leads of the source coil 308a to a power source (not shown) such that a current flows through the source coil 308a and a magnetic field is induced. The induced magnetic field may interact with the magnet 308b to cause vibration in the tube 302. Conversely, the controller 312 may function to measure vibration in the tube 302 by receiving current induced in the sensor coil 310a by radial displacement of the magnet 310b with respect to the sensor coil 310a.

The sensor 300 may further comprise a temperature sensor 314 that may be configured to measure the temperature of a fluid sample within the sensor 300. Example temperature sensors include, but at not limited to, thermistors and resistance temperature detectors. As depicted, the temperature sensor 314 is coupled to the housing 304 and in fluid communication with the internal bore 302a of the tube 302. Leads of the temperature sensor 314 may be coupled to the controller 312. As a fluid sample is introduced into the tube 302, the temperature sensor 314 may identify the temperature of the fluid, or may generate an output (e.g., a change in resistance) from which the controller 314 may determine the temperature of the fluid. Other types and configurations of temperature sensors may be used within the context of the sensor 300 and tube 302.

In use, a fluid sample may be introduced and/or allowed to flow through the bore 302a of the tube 302, and the controller 312 may signal the vibration source 308 to cause and abruptly release a lateral displacement in the tube 302. The abrupt release may cause the tube 302 to vibrate at a resonant frequency. The vibration receiver 310 may measure the lateral movement of the tube 302 over time in the form of an induced current or voltage at the coil 310a, and that measurement may be recorded, for instance, at the controller 312, or transmitted to another controller or information handling system for recordation/storage.

Figure 4A:
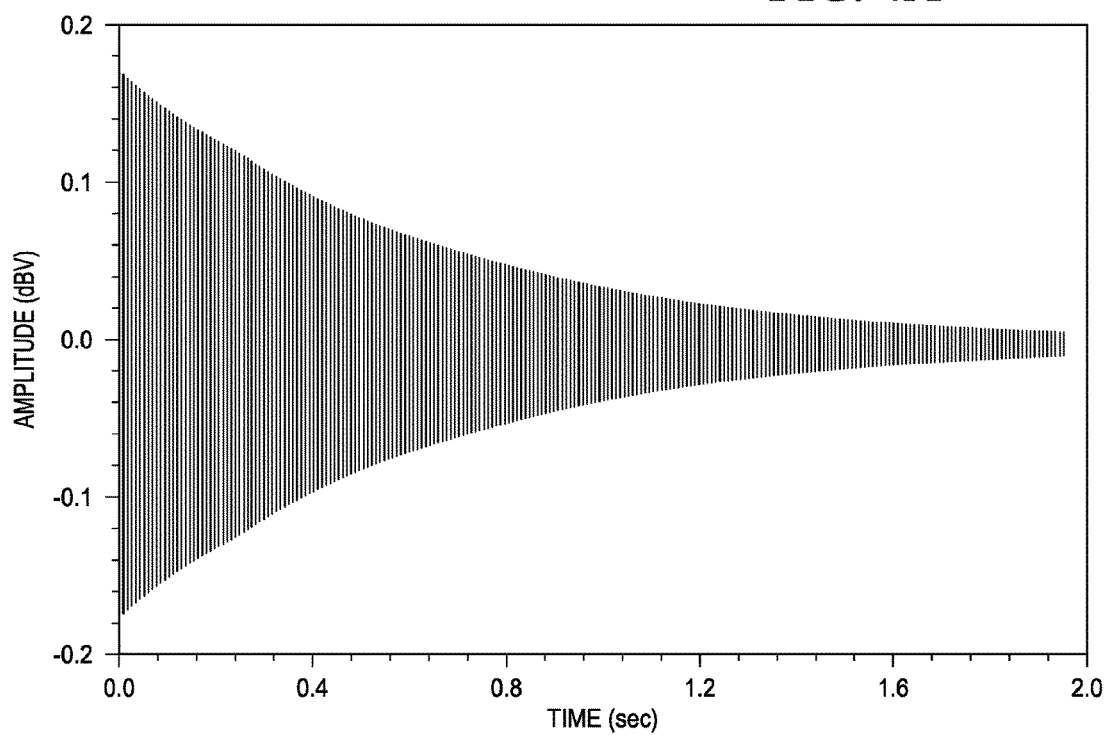
FIGS. 4A and 4B are amplitude and frequency charts generated from example measurements captured by a vibrating sensor, according to aspects of the present disclosure.
Figure 4B:
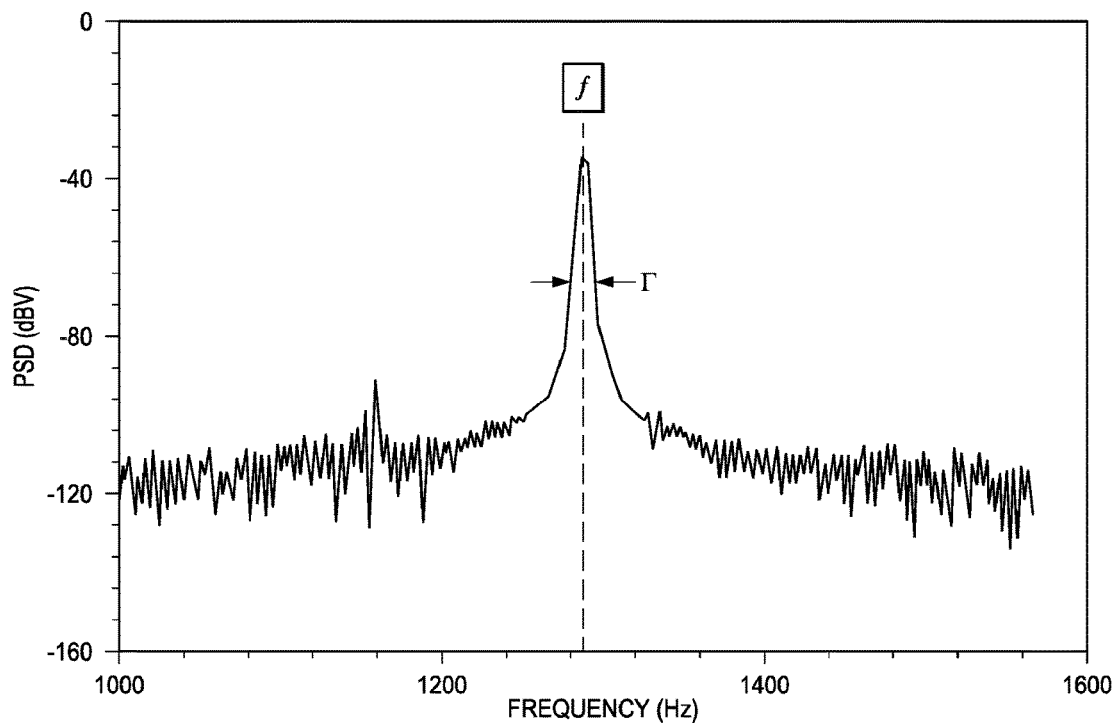

The measurements from the vibration receiver 310 may be analyzed to determine one or more vibration characteristics of the tube 302 and the fluid sample within. Example vibration characteristics include, but are not limited, the amplitude attenuation of the lateral deflections measured by the vibration receiver 310 and the resonant frequency at which the tube 302 vibration. To illustrate, FIGS. 4A and 4B are charts generated from example measurements captured by vibration receiver 310 of sensor 300. Specifically, FIG. 4A illustrates a signal 400 representing the amplitude in decibels of measured lateral deflections of tube 302 over time t, and FIG. 4B illustrates a frequency-domain signal representation 450 of the signal 400. The frequency-domain signal representation 450 may be generated, for example, using a fast Fourier transform or other transformations that would be appreciated by one of ordinary skill in the art in view of this disclosure.

As can be seen in FIG. 4A, when a discrete vibration excitation from a vibration source is used, the initial lateral deflection may have the greatest amplitude, with the amount of lateral displacement and thereby amplitude of the subsequent lateral deflections attenuating over time. The attenuation may be expressed using the equation $A(t) = A(0)e^{-\alpha t}$, where $A(0)$ represents the amplitude of the initial lateral deflection triggered by the vibration source, $\alpha$ comprises a decay parameter that depends, in part, on the viscosity of the fluid sample and material properties of the tube, and $t$ represents time.

The resonant frequency of the vibration may depend, in part, on material properties of the vibrating tube and the density of the fluid sample, and may be identified in the frequency-domain signal 450 of FIG. 4B. Specifically, the resonant frequency may comprise the dominant frequency in the frequency-domain signal 450 may be represented by a peak 452 centered on the resonant frequency f. In certain embodiments, a width $\Gamma$ of the resonant frequency peak 452 may further be used to characterize the vibration. The width $\Gamma$ may be determined, for instance, at a point on the peak 452 that is some set interval below the maximum amplitude, or at a point such that the energy represented by the peak 452 above the width point represents a set percentage of the overall energy within the signal.

According to aspects of the present disclosure, some or all of the vibration characteristics described above may be used to determine one or more thermo-physical properties of a fluid sample, depending on the configuration of the vibrating sensor. For instance, a vibrating sensor configured similarly to the sensor described above with reference to FIG. 3 may comprise a fluid density and viscosity sensor that is operable to determine the density and viscosity of a fluid sample based, at least in part, on a resonant frequency of the vibration at the tube 302 as well as a resonant frequency peak width $\Gamma$. With respect to the density of the fluid sample, a mass density $\rho$ of the fluid may be determined based, at least in part, on the following equation:

$$f(\rho, T) = f(0) * \left[ 1 + 1 \Big/ \left( 2\left(1 - \left(\frac{a}{b}\right)^2\right) * \frac{\rho}{\rho_t} \right) \right]$$

where $f(\rho,T)$ comprises the measured resonant frequency, $f(0)$ corresponds to a resonant frequency of the vibrating tube under vacuum conditions, T comprises a temperature of the fluid sample, a corresponds to an outside diameter of the vibrating tube, b corresponds to an inside diameter of the vibrating tube, and $\rho_t$ corresponds to a mass density of the vibrating tube. The variables $f(0)$, a, b, and $\rho_t$ may be known or otherwise determined while the sensor is being constructed so that mass density $\rho$ of the fluid represents the only unknown. The mass density $\rho$ of the fluid may be determined at a controller coupled to the sensor, for instance, using stored values for the variables, or the measured current signal may be stored within the controller or transmitted to the surface for a later determination of the resonant frequency and the corresponding mass density p of the fluid.

Figure 5:
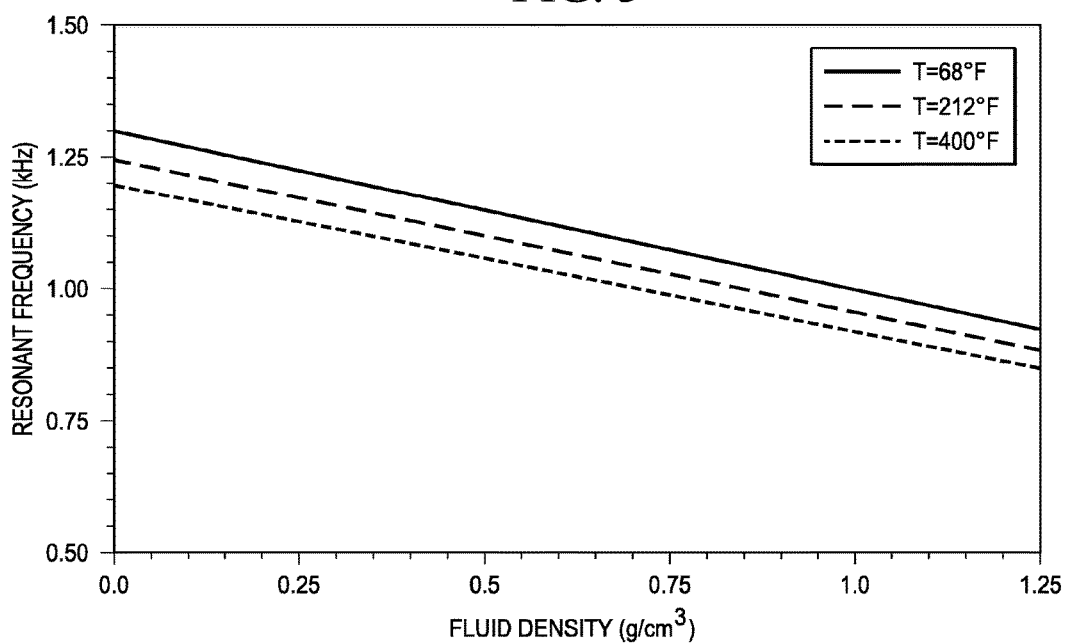
FIG. 5 is a chart illustrating an example temperature-dependent resonant frequency response of a vibrating sensor, according to aspects of the present disclosure.

FIG. 5 is a chart illustrating an example temperature-dependent resonant frequency response of a vibrating sensor when that sensor is filled with fluids of differing densities. As can be seen, the resonant frequency of the sensor may generally decrease when the density of the fluid sample increases. The chart also identifies a temperature component, in which the resonant frequency corresponding to a given fluid density is lower when the temperature of the fluid is higher. With knowledge of the resonant frequency from a vibration sensor, and the temperature of a fluid sample from a temperature sensor, example vibrating sensors similar to those described with reference to FIG. 3 may be used to accurately calculate the fluid density of the fluid sample.

Viscosity of the fluid sample may be analyzed according to a simplified light-damped mechanical system, with the viscosity, in addition to the material properties of the vibrating tube, primarily affecting the resonant frequency peak width $\Gamma$. In certain embodiments, viscosity of the fluid sample may be correlated to or otherwise determined using the width $\Gamma$. For instance, the viscosity may be determined using a quality factor Q that may equal the resonant frequency f of the vibrating tube with the fluid sample divided by the resonant frequency peak width $\Gamma$. The overall quality factor Q may include contributions from both the material properties of the vibrating tube and the viscosity of the fluid sample. The viscosity of the fluid sample may be correlated with its contribution, $Q_{Fluid}$, to the quality factor Q, which may be calculated using the following equation $$\frac{1}{Q} = \frac{1}{Q_{Fluid}} + \frac{1}{Q_{Sensor}}$$

where $Q_{Sensor}$ represents the quality factor contribution of the sensor/vibrating tube. Alternatively, or in addition, the viscosity of the fluid sample may also be correlated with its contribution, $\Delta\Gamma_{Fluid}$, to the resonant frequency peak width $\Gamma$, which may be determined using the following equation $$\Delta\Gamma_{Fluid} = \Gamma - \Gamma_{Sensor}(T)$$

where $\Gamma_{Sensor}(T)$ represents the width contribution of the sensor/vibrating tube as a function of temperature in vacuum conditions. The temperature dependent frequency response of the sensor/vibrating tube in vacuum conditions may be measured and determined during manufacturing of the sensor, such that the correct value may be selected based on temperature input from the sensor to correctly calculate the width contribution of the fluid sample.

Figure 6:
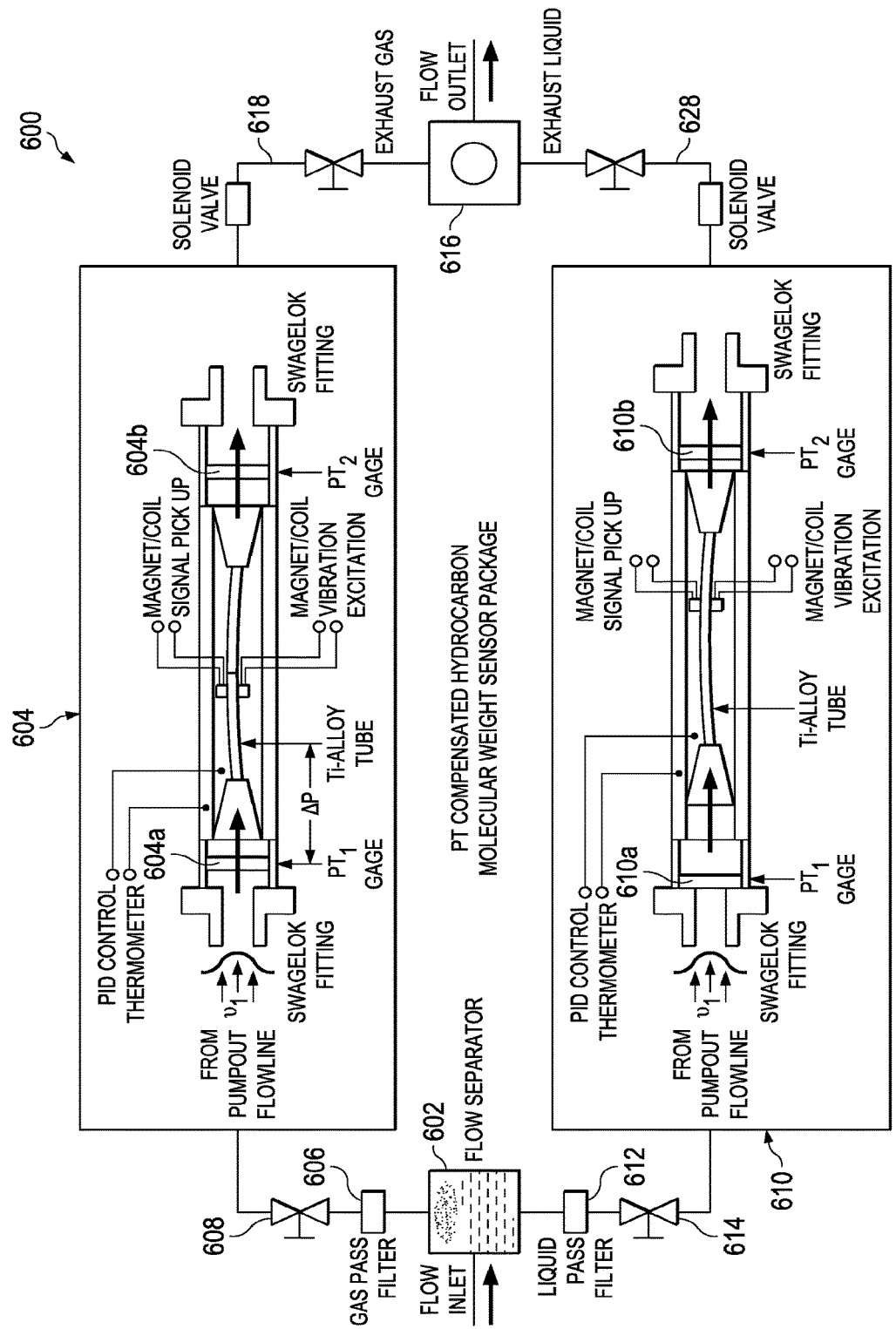
FIG. 6 is a diagram illustrating an example molecular weight sensor incorporating at least one vibrating sensor, according to aspects of the present disclosure.

As stated above, vibrating sensors may be incorporated into purpose-built sensors to measure or determine one or more thermo-physical properties. In contrast to the sensor described above with respect to FIG. 3, which may be configured to measure fluid density and velocity, FIG. 6 is a diagram illustrating an example molecular weight sensor 600 incorporating at least on vibrating sensor, according to aspects of the present disclosure. The sensor 600 comprises a flow separator 602 in fluid communication with a fluid sample. An example flow separator 602 includes, but is not limited to, a gravity separator, a centrifugal separator, and a piston pump. The flow separator 602 may be in fluid communication with a vibrating sensor 604 through a gas-pass filter 606 and a valve 608 that allows a gas phase of a fluid sample separated within the separator 602 to reach the sensor 604. The flow separator 602 may be in fluid communication with a vibrating sensor 610 through a liquid-pass filter 612 and a valve 614 that allows a liquid phase of a fluid sample separated within the separator 602 to reach the sensor 610. The vibrating sensors 604 and 610 may be in selective fluid communication with a flow outlet 616 through respective solenoid valves 614 and 616.

As depicted, the vibrating sensors 604 and 610 comprise a similar configuration function similarly to each other and the vibrating sensor described above with reference to FIG. 3. The vibrating sensors 604 and 610 differ, however, in the inclusion of pressure and temperature gauges 604a/604b and 610a/610b before and after the respective vibrating tubes. Additionally the vibrating sensors 604 and 610 comprise swage lock fittings to allow easy coupling to one or more fluid systems that extract and provide the fluid samples. Although not depicted, the sensor 600 may comprise one or more controllers that may be coupled to the vibration sources and receivers, and pressure and temperature gauges 604a/604b and 610a/610b of the vibrating sensors 604 and 610.

In use, a formation fluid sample may be extracted from a formation and introduced into the separator 602. Typically, formation fluid samples may comprise a gas phase suspended within a liquid phase. The separator 602 may separate the gas phase from the liquid phase, introduce the gas phase into vibrating sensor 604, and introduce the liquid phase into vibrating sensor 610. Once inside the vibrating sensor 604, the pressure and temperature gauges 604a/604b may measure the pressure and temperature of the gas phase, and the vibrating sensor 604 may drive vibrations and measure lateral displacements from which the resonant frequency of the vibrating sensor 604 and the mass density of the gas phase can be determined, using techniques similar to those described above. Based on the determined mass density of the gas phase, its molecular weight may be determined using the following equation $$MW_{Gas} \approx \rho(P, T) * \frac{RT}{P}$$

where P comprises the pressure measured at the pressure and temperature gauges 604a/604b; T comprises the temperature measured at the pressure and temperature gauges 604a/604b; R comprises the universal molecular gas constant; and $\rho(P,T)$ comprises the mass density of the gas phase at pressure P and temperature T. In certain embodiments, the mass density of the gas phase may be determined from measurements performed at a previous sensor, such the sensor described above with reference to FIG. 3, so that the mass density does not have to be separately determined within the sensor 600.

Once inside the vibrating sensor 610, the pressure and temperature gauges 610a/610b may measure the pressure and temperature of the liquid phase, and the vibrating sensor 610 may drive vibrations and measure lateral displacements from which the resonant frequency of the vibrating sensor 610 and the mass density of the liquid phase can be determined, using techniques similar to those described above. Determining the molecular weight of the liquid phase may start from the following equation of state for wide ranges of pressure and temperature calculates of phase equilibrium in non-polar and polar fluids:

$$Z = \frac{PV}{RT} = \frac{V}{V-b} - \frac{\alpha(T)}{RT(V+b)}$$

where V comprises a volume; $\alpha(T)$ corresponds to an attractive force between molecules; and b comprises a co-volume occupied by molecules that is proportional to its molecular weight. Based, at least in part, on the above equation of state, the liquid-phase molecular weight can be approximated using the following equation $$MW \approx \frac{\rho(P, T, b) * RT}{P}\left[1 + \frac{\alpha(T)}{RTV} + \left(1 - \frac{\alpha(T)}{RTV}\right) * \frac{b}{V}\right]$$

where $\rho(P,T,b)$ comprises the mass density of the liquid phase determined using the vibrating sensor. The calculations may be performed, for instance, at a downhole controller coupled to or integrated with the sensor 600; at remote information handling system using measurements and information generated and stored at the sensor or a controller coupled to the sensor; and/or at remote information handling system using measurements and information transmitted to the information handling system in real or near-real time.

Figure 7:
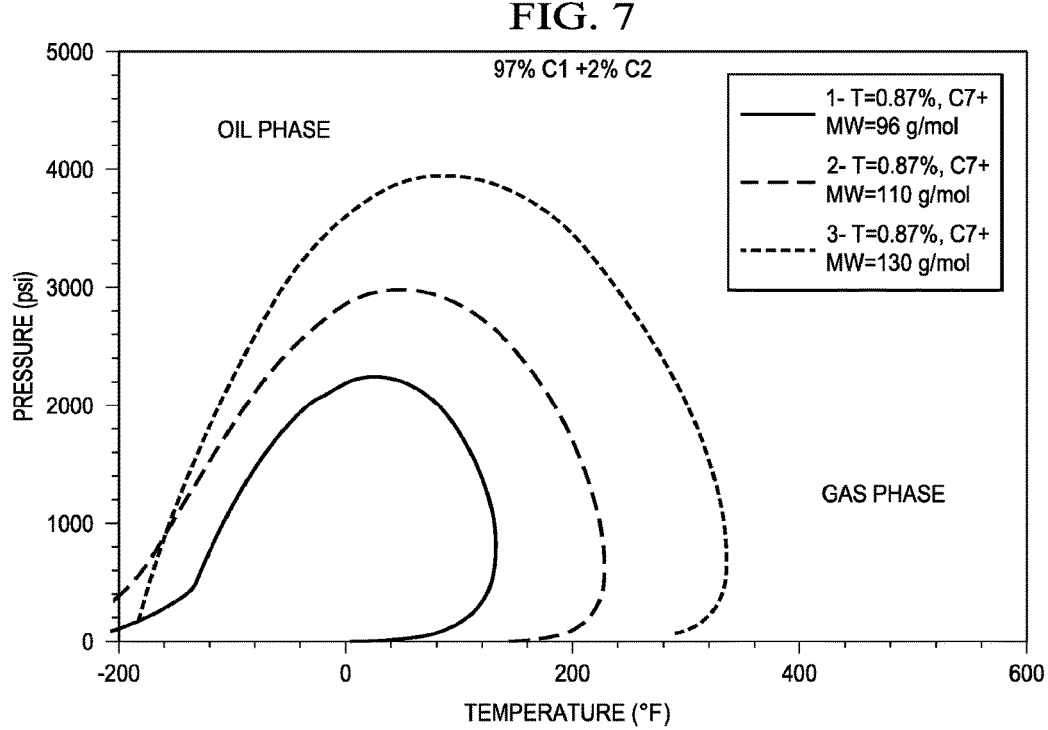
FIG. 7 is a chart illustrating a pressure-temperature chart for simulated fluid measurements, according to aspects of the present disclosure.

The molecular weight measurements described above may be used to identify naturally occurring hydrocarbon gas reservoirs and predict possible phase behavior of reservoir fluid. FIG. 7 is an example pressure-temperature phase envelope diagram under three different gas molecular weights. Specifically, FIG. 7 illustrates a simulation that assumes a fluid composition of 97% C1 ($CH_4$, Methane, MW=16.04 Dalton), and 2% C2 ($C_2H_6$, Ethane, MW=30.07 Dalton) with 0.82% C7+ hydrocarbons. In reality, 0.87% C7+ may have different molecular weights such as from 90 to a few hundred Daltons. In one case, a gas reservoir may consist primarily of C1-C4 hydrocarbon gas but the 0.82% C7+ may have an averaged molecular weight of 97 Dalton; in second case, the 0.82% C7+ may have an averaged molecular weight of 110 Dalton, in third case, the 0.82% C7+ may have an averaged molecular weight of 130 Dalton. Although the averaged gas molecular weight only changes from 18.293, 18.402, to 18.566 Dalton, the PT phase envelop diagram, as shown in FIG. 7, has changed dramatically. The high carbon bonded hydrocarbons of C7-C30 may have limited content as wet gas, which is saturated with ~1% volume of liquid hydrocarbons, but the gas molecular weight increase could indicate the corresponding PT phase envelop change, which may have high impact either on well completion design or asset management.

The measurement of gas molecular weight also can help to understand the transport properties of hydrocarbons from different layer of subsurface formation. For instance, the increase of the water will decrease measured averaged gas molecular weight. Also, heavy oil evaporated gas could increase gas molecular weight because of localized geothermal anomalies. In another instance, carbon dioxide may become rich due to specific geological regions. These hydrocarbon gas composition change will modify a well's PT phase envelop diagram. The simulation has shown that the critical point and gas/liquid due-point curve can be changed by the gas molecular weight increase.

Figure 8:
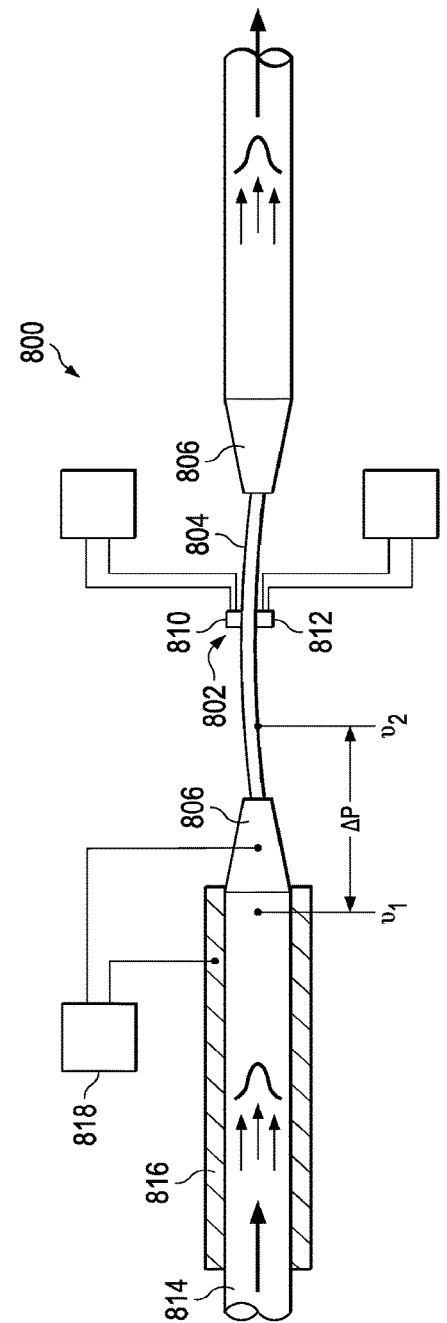
FIG. 8 is a diagram illustrating an example thermal conductivity and heat capacity sensor incorporating at least one vibrating sensor, according to aspects of the present disclosure.

Other types of thermo-physical sensors also may incorporate vibrating sensors according to aspects of the present disclosure. FIG. 8 is a diagram illustrating an example thermal conductivity and heat capacity sensor 800 incorporating at least one vibrating sensor, according to aspects of the present disclosure. As depicted, the sensor 800 includes a vibrating sensor 802 comprising a tube 804 coupled between two anchors 806 and 808. The vibrating sensor 802 further comprises a vibration source 810 and a vibration receiver 812 coupled to a controller (not shown). The vibration receiver 812 may aide in the determination of a resonant frequency of the tube 804 when the tube 804 contains a fluid sample, similar to the functionality of the vibrating sensors described above.

As depicted, the sensor 800 includes a fluid conduit 814 in fluid communication with an internal bore of the tube 804 and through which a fluid sample may be introduced into the tube 804. The sensor 800 further comprises a heating element 816 surrounding or otherwise adjacent to the fluid conduit 814 that may heat a fluid sample before it is introduced into the tube 804. As depicted, the heating element 816 comprises a heat pump. A controller 818 may be coupled may be coupled to and control the thermal energy output by the heating element 816. In certain instances, the controller 818 may function to vary the thermal energy output by the heating element 816 to cause a fluid sample within the fluid conduit 814 to reach a predetermined temperature. The controller 818 may be coupled to a temperature sensor 820 in fluid communication with the conduit 814 and that provides a temperature feedback signal to the controller 818 from which the controller 818 may control the heating element 816.

In use, a fluid sample may be introduced into the fluid conduit 814 and heated. The fluid sample then may be introduced into the tube 804, where the vibration source 810 and vibration receiver 812 may cause vibrations in the tube 802 from which a resonant frequency can be determined using processes similar to those described above. Temperature changes in the fluid sample may lead to shifts in the resonant frequency determined using measurements by the vibration receiver 812. When the heating element 816 is time modulated, the speed with which the thermal energy from heating element 816 dissipates into the fluid sample and changes the temperature of the fluid depends, in part, on the thermal conductivity of the fluid sample. Specifically, the time interval $\Delta\tau$ from heat pumping to a shift in the measured resonant frequency of the tube 804 and fluid sample may be proportional to a thermal conductivity parameter k of the fluid sample, with a higher thermal conductivity corresponding to a shorter transient time for observing a change in the resonant frequency.

The relative shift of the resonant frequency may be linear with the temperature T of the fluid sample and represented by the equation $f(T)=(0)+\xi*T$, where $f(T)$ corresponds to the resonant frequency at temperature T; $f(0)$ corresponds to the resonant frequency of the vibrating tube; and $\xi$ corresponds to a sensitivity of the sensor 800. Accordingly, determining the resonant frequency change may provide the fluid temperature change, and the amount of time needed for the fluid to reach a specific temperature may provide the thermal conductivity parameter k. Since fluid temperature increase is generally non-linear, the thermal conductivity parameter k may be expressed by the following polynomial function $$k=k(T0)+A*\Delta\tau+B*\Delta\tau^2+\ldots$$

where $\Delta\tau$ comprises the transient response time corresponding to a change in the resonant frequency; and k(T0), A, and B comprise calibration constants.

Heat capacity of the fluid sample in the sensor 800 may also be determined based on changes in the fluid temperature and the resonant frequency of the tube 804. The heat capacity $C_p$ of the fluid sample generally may be related to a thermodynamic process and thermal energy transport from the heating element 816 to the fluid sample. When the heating element 816 comprises a heat pump, for instance, the electrical current I driving the heat pump may provide a thermal energy E that is related to the current I and the resistance Rs of the heating element. For two transient thermal pumping events that lead to fluid temperature changes from $T_1$ to $T_2$, the thermodynamic process may be described using the following two equations $$E_1=m*C_p*T_1=\rho*V*C_p*T_1$$

$$E_2=m*C_p*T_2=\rho*V*C_p*T_2$$

where the fluid mass variation during the two thermal events has been ignored for a limited time internal. Based on the above, the thermal capacity may be calculated using the following equation $$C_p(T) \approx \frac{E_1-E_2}{[(T_1-T_2)*m]} = \Delta I^2(t)*Rs/[m*\xi*\Delta f]$$

where $\Delta f$ comprises the resonant frequency variation, and the fluid mass ($m=\rho*V$) and sensor sensitivity $\xi$ are constant.

In certain embodiments, some or all of the thermo-physical characteristics determined using the sensors described above, e.g., fluid density $\rho(T)$, thermal conductivity $k(T)$, and heat capacity $C_p(T)$ may be used to calculate one or more other thermo-physical characteristics to provide more robust in situ characteristics. For instance, the mass diffusivity e(T) of a fluid sample may be determined using the following equation $$e(T)=\sqrt{k(T)+C_p(T)+\rho(T)}$$

These additional calculations may be made, for instance, at one or more controllers coupled to the sensor and/or at one or more surface information handling systems or controllers using information transmitted from the downhole sensors in real or near-real time, or using information retrieved at a later time.

Figure 9:
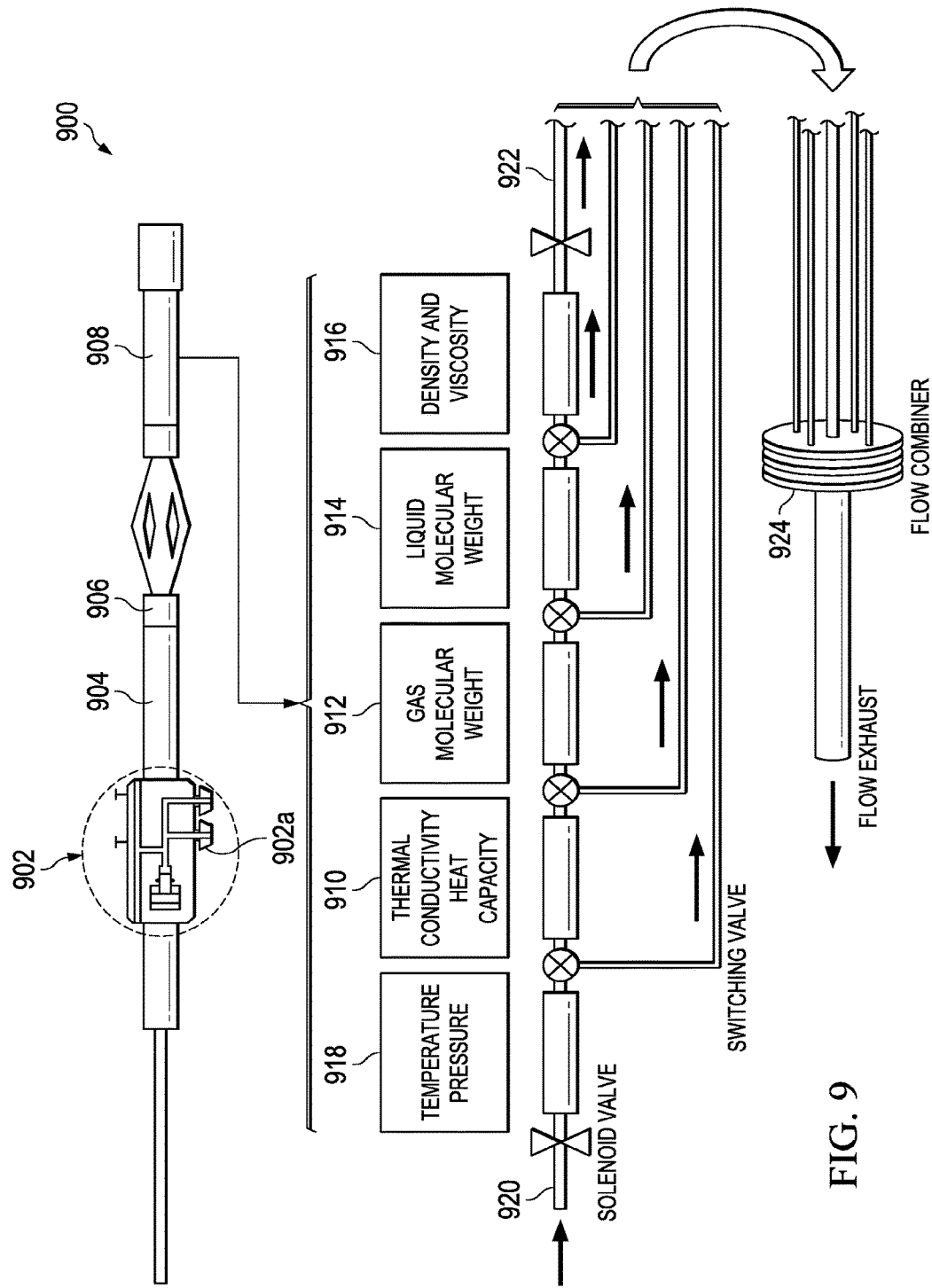
FIG. 9 is a diagram illustrating an example downhole wireline logging tool in which thermo-physical sensors incorporating one or more vibrating sensors have been incorporated, according to aspects of the present disclosure.

In certain embodiments, thermo-physical sensors incorporating one or more vibrating sensors, including those thermo-physical sensors described above, may be modularized and/or incorporated as a suite of sensors into existing downhole logging tools. FIG. 9 is a diagram illustrating an example downhole wireline logging tool 900 in which thermo-physical sensors incorporating one or more vibrating sensors have been incorporated. As depicted, the tool 900 comprises a fluid pump-out system 902 comprising one or more extendable pads 902a through which fluid samples may be extracted from a formation and provided to other portions of the tool 900. The tool 900 may further comprise one or more sub-tools or modules 904, 906, and 908 of a type that may depend on the types of measurements to be generated by the logging device. For instance, the modules 904 and 906 may comprise optical sensor modules, ultrasonic sensor modules with or without caliper support, power supplies, telemetry modules, etc.

The module 908 comprises a suite of thermo-physical sensors incorporating one or more vibrating sensors similar to those described above. For instance, the module 908 comprises a thermal conductivity and heat capacity sensor 910, a gas molecular weight sensor 912, a liquid molecular weight sensor 914, and a density and viscosity sensor 916. The module 908 further comprises a dedicated temperature and pressure gauge 918. As depicted, the thermo-physical sensors 908-916 are in fluid communication with a flow inlet 920, which may, for instance, be in fluid communication with the pump-out system 902, which may provide fluid samples to the module 908. A flow outlet 922 may receive the fluid sample after is has passed through the module 908.

The thermo-physical sensors 908-916 may be coupled in series through a plurality of intermediate flow switch valves, forming a primary flow channel from the flow inlet 920 to the flow outlet 922. The order and orientation of the sensors 908-916 and flow switch valves, however, are not intended to be limited. As depicted, each an intermediate flow switch valves may provide a secondary flow channel between the sensors 908-916 and a flow combiner 924 that may be positioned at an end of the module 908. The flow switch valve/secondary flow channel in front of each of the sensors 908-916 with respect to the direction of fluid flow through the module 908 may allow for each sensor to be replaceable or down selectable. The flow combiner 924 may receive fluid from the flow outlet 922 and the secondary flow channels and combined the fluid into a single flow exhaust 926, through which the fluid may be provided to an additional module or expelled from the tool 900.

In use, each of the sensors 908-916 may work independently, and may be controlled by dedicated controllers that may be communicably coupled to a telemetry system of the tool 900. In other embodiments, each of the sensors 908-916 may have dedicated controllers that receive instructions from a supervisory controller (not shown) that directs the signals the dedicated controllers and receives measurements from the dedicated controllers. The supervisory controller may be communicably coupled to a telemetry system of the tool 900. In yet other embodiments, a single controller may be shared between all of the sensors 908-916 and directly control the operation of each of the sensors.

Modifications, additions, or omissions may be made to FIG. 9 without departing from the scope of the present disclosure. For instance, FIG. 9 illustrates a wireline logging tool with thermo-physical sensors in a particular configuration, but other configurations are possible. Additionally, the logging tool may be adapted for LWD/MWD applications and maintain the modularity and general functionality described above. Furthermore, fewer, additional, and or different types of components and sensors beyond those illustrated may be included in the logging tool without departing from the scope of the present disclosure.

Embodiments disclosed herein include:
A. A downhole tool including a tube including an inner bore that receives a sample of fluid from a subterranean formation. The downhole tool also includes a vibration source at least partially coupled to the tube and a vibration receiver at least partially coupled to the tube. The downhole tool further includes a controller coupled to the vibration source and the vibration receiver.
B. A method including obtaining a fluid sample from a subterranean formation with a downhole tool positioned within a borehole in the subterranean formation. The method also includes introducing the fluid sample into the inner bore of a tube within the downhole tool, inducing a vibration in the tube, and measuring the induced vibration in the tube. The method further includes determining a resonant frequency of the vibration and determining a thermo-physical property of the fluid sample based, at least in part, on the determined resonant frequency.
C. A downhole tool including a fluid pump-out system to obtain a sample of fluid from a subterranean formation. The downhole tool also includes a sensor in fluid communication with the pump-out system to determine density and viscosity of the fluid sample, a sensor in fluid communication with the pump-out system to determine thermal conductivity and heat capacity of the fluid sample, and a sensor in fluid communication with the pump-out system to determine hydrocarbon molecular weight of the fluid sample. At least one of the density and viscosity sensor, the thermal conductivity and heat capacity sensor, and the hydrocarbon molecular weight sensor includes: a tube including an inner bore that receives a sample of fluid from a subterranean formation, a vibration source at least partially coupled to the tube, a vibration receiver at least partially coupled to the tube, and a controller coupled to the vibration source and the vibration receiver.

Each of the embodiments A, B, and C may have one or more of the following additional elements in combination: Element 1: further including a housing in which the tube is at least partially positioned. Element 2: wherein the vibration source includes a source magnet coupled to the tube and a source coil coupled to the housing and axially aligned with the source magnet, and the source coil is coupled to the controller. Element 3: wherein the vibration receiver includes a receiver magnet coupled to the tube and a receiver coil coupled to the housing and axially aligned with the receiver magnet, and the receiver coil is coupled to the controller. Element 4: wherein the vibration source, in response to a signal from the controller, induces a vibration in the tube, and the vibration receiver measures the lateral displacement of the tube over time during the induced vibration of the tube. Element 5: wherein the controller receives the lateral displacement measurements from the vibration receiver and determines a resonant frequency of the vibration. Element 6: further including a temperature sensor in fluid communication with the inner bore of the tube and communicably coupled to the controller. Element 7: further including a heating element coupled to a fluid conduit in fluid communication with the inner bore of the tube. Element 8: further including a liquid-gas separator in fluid communication with the inner bore of the tube.

Element 9: wherein the downhole tool includes one of a wireline logging tool and a logging-while-drilling tool. Element 10: wherein the thermo-physical property of the fluid sample includes at least one of density, viscosity, thermal conductivity, heat capacity, and hydrocarbon molecular weight. Element 11: wherein determining the resonant frequency of the vibration includes determining a frequency-domain representation of the induced vibration measurement. Element 12: wherein determining the viscosity of the fluid sample includes determining a width of a peak in the frequency-domain representation corresponding to the determined resonant frequency. Element 13: wherein determining the thermal conductivity and heat capacity of the fluid sample includes heating the fluid sample and determining a resonant frequency shift. Element 14: wherein determining the hydrocarbon molecular weight includes separating the fluid sample into a gas phase and a liquid phase and determining a resonant frequency corresponding to the gas phase and a resonant frequency corresponding to the liquid phase.

Element 15: wherein the downhole tool includes one of a wireline logging tool and a logging-while-drilling tool. Element 16: wherein the downhole tool further includes at least one of an optical sensor tool and a ultrasonic sensor tool. Element 17: wherein the vibration source, in response to a signal from the controller, induces a vibration in the tube, and the vibration receiver measures the lateral displacement of the tube over time during the induced vibration of the tube.

Therefore, the present disclosure is well-adapted to carry out the objects and attain the ends and advantages mentioned as well as those which are inherent therein. While the disclosure has been depicted and described by reference to exemplary embodiments of the disclosure, such a reference does not imply a limitation on the disclosure, and no such limitation is to be inferred. The disclosure is capable of considerable modification, alteration, and equivalents in form and function, as will occur to those ordinarily skilled in the pertinent arts and having the benefit of this disclosure. The depicted and described embodiments of the disclosure are exemplary only, and are not exhaustive of the scope of the disclosure. Consequently, the disclosure is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A downhole tool, comprising:
   a tube comprising an inner bore that receives a gas phase of a sample of fluid from a subterranean formation;
   a vibration source at least partially coupled to the tube;
   a vibration receiver at least partially coupled to the tube;
   a controller coupled to the vibration source and the vibration receiver;
   a second tube comprising an inner bore that receives a liquid phase of the sample of fluid from the subterranean formation; and
   a liquid-gas separator in fluid communication with the inner bore of the tube and the inner bore of the second tube.

2. The downhole tool of claim 1, further comprising a housing in which the tube is at least partially positioned.

3. The downhole tool of claim 2, wherein
   the vibration source comprises a source magnet coupled to the tube and a source coil coupled to the housing and axially aligned with the source magnet; and
   the source coil is coupled to the controller.

4. The downhole tool of claim 3, wherein
   the vibration receiver comprises a receiver magnet coupled to the tube and a receiver coil coupled to the housing and axially aligned with the receiver magnet; and
   the receiver coil is coupled to the controller.

5. The downhole tool of claim 1, wherein
   the vibration source, in response to a signal from the controller, induces a vibration in the tube; and
   the vibration receiver measures the lateral displacement of the tube over time during the induced vibration of the tube.

6. The downhole tool of claim 5, wherein the controller receives the lateral displacement measurements from the vibration receiver and determines a resonant frequency of the vibration.

7. The downhole tool of claim 5, further comprising a temperature sensor in fluid communication with the inner bore of the tube and communicably coupled to the controller.

8. The downhole tool of claim 5, further comprising a heating element coupled to a fluid conduit in fluid communication with the inner bore of the tube.

9. A method, comprising:
   obtaining a fluid sample from a subterranean formation with a downhole tool positioned within a borehole in the subterranean formation;
   introducing the fluid sample into the inner bore of a tube within the downhole tool;
   inducing a vibration in the tube;
   measuring the induced vibration in the tube;
   determining a resonant frequency of the vibration; and
   determining a thermo-physical property of the fluid sample based, at least in part, on the determined resonant frequency, wherein the thermo-physical property of the fluid sample comprises at least one of density, viscosity, thermal conductivity, heat capacity, or hydrocarbon molecular weight, wherein determining the thermo-physical property of the fluid sample comprises determining the hydrocarbon molecular weight by:
   separating the fluid sample into a gas phase and a liquid phase; and
   determining a resonant frequency corresponding to the gas phase and a resonant frequency corresponding to the liquid phase.

10. The method of claim 9, wherein the downhole tool comprises one of a wireline logging tool and a logging-while-drilling tool.

11. The method of claim 9, wherein determining the resonant frequency of the vibration comprises determining a frequency-domain representation of the induced vibration measurement.

12. The method of claim 11, wherein determining the viscosity of the fluid sample comprises determining a width of a peak in the frequency-domain representation corresponding to the determined resonant frequency.

13. The method of claim 11, wherein determining the thermal conductivity and heat capacity of the fluid sample comprises heating the fluid sample and determining a resonant frequency shift.

14. A downhole tool, comprising
   a fluid pump-out system to obtain a sample of fluid from a subterranean formation;
   a sensor in fluid communication with the pump-out system to determine density and viscosity of the fluid sample;
   a sensor in fluid communication with the pump-out system to determine thermal conductivity and heat capacity of the fluid sample; and
   a sensor in fluid communication with the pump-out system to determine hydrocarbon molecular weight of the fluid sample;
   wherein at least one of the density and viscosity sensor, the thermal conductivity and heat capacity sensor, and the hydrocarbon molecular weight sensor comprises
   a tube comprising an inner bore that receives a sample of fluid from a subterranean formation;
   a vibration source at least partially coupled to the tube;
   a vibration receiver at least partially coupled to the tube; and
   a controller coupled to the vibration source and the vibration receiver.

15. The downhole tool of claim 14, wherein the downhole tool comprises one of a wireline logging tool and a logging-while-drilling tool.

16. The downhole tool of claim 15, wherein the downhole tool further comprises at least one of an optical sensor tool and an ultrasonic sensor tool.

17. The downhole tool of claim 14, wherein
the vibration source, in response to a signal from the controller, induces a vibration in the tube; and
the vibration receiver measures the lateral displacement of the tube over time during the induced vibration of the tube.

18. The downhole tool of claim 1, further comprising:
a second vibration source at least partially coupled to the second tube; and
a second vibration receiver at least partially coupled to the tube.

19. The downhole tool of claim 14, wherein the hydrocarbon molecular weight sensor comprises
a first tube comprising an inner bore that receives a gas phase of the sample of fluid from the subterranean formation;
a vibration source at least partially coupled to the first tube;
a vibration receiver at least partially coupled to the first tube;
a second tube comprising an inner bore that receives a liquid phase of the sample of fluid from the subterranean formation; and
a liquid-gas separator in fluid communication with the inner bore of the first tube and the inner bore of the second tube.

20. The downhole tool of claim 19, wherein the hydrocarbon molecular weight sensor further comprises:
a second vibration source at least partially coupled to the second tube; and
a second vibration receiver at least partially coupled to the second tube.

* * * * *